United States Patent [19]

Discko, Jr.

[11] Patent Number: 5,106,297

[45] Date of Patent: Apr. 21, 1992

[54] DENTAL BONDING LIQUID AND SEALANT TRAY

[75] Inventor: John Discko, Jr., Hamden, Conn.

[73] Assignee: Centrix, Inc., Milford, Conn.

[21] Appl. No.: 600,748

[22] Filed: Oct. 22, 1990

[51] Int. Cl.$^5$ .............................................. A61G 15/00
[52] U.S. Cl. .................................. 433/77; 206/63.5; 206/564
[58] Field of Search .................. 433/25, 49, 77, 79, 433/163, 229; 206/63.5, 1.8, 368, 369, 562, 563, 564; 220/514, 555

[56] References Cited

U.S. PATENT DOCUMENTS

| | | | |
|---|---|---|---|
| 1,659,315 | 2/1928 | Dailey | 433/79 |
| 1,704,122 | 3/1929 | Cohen | 433/79 |
| 3,469,686 | 9/1969 | Gutsche et al. | 206/564 |
| 4,294,349 | 10/1981 | Ibsen et al. | 206/63.5 |
| 4,852,738 | 8/1989 | Craig et al. | 206/63.5 |

FOREIGN PATENT DOCUMENTS 0240685 10/1987 European Pat. Off. .............. 433/25

Primary Examiner—Cary E. O'Connor
Attorney, Agent, or Firm—Paul A. Fattibene; Arthur T. Fattibene

[57] ABSTRACT

A dental tray having depressions therein for holding a bottle of dental material upside down and having wells of distinctive shape and configuration. An inexpensive disposable tray is disclosed for use in preparing single or multiple component bonding liquids and sealants. Multiple depressions configured to hold a bottle having a cap with a shoulder upside down are formed within the tray so the dentist can readily dispense the single or multiple component bonding liquids and sealants. Distinctively shaped wells are positioned in line with the depressions holding the bottle upside down preventing confusion between the multi-part dispensed bonding liquids and sealants. A finger indentation in the side opposite the depressions is provided to facilitate holding the lightweight tray during mixing or use, as well as to further provide a divided fuel to the tray preventing confusion between the dispensed component parts of the multiple component bonding liquids and sealants.

12 Claims, 3 Drawing Sheets

ROTATE 90°

DENTAL BONDING LIQUID AND SEALANT TRAY

FIELD OF THE INVENTION

This invention relates generally to a tray for dental materials, and more particularly to an inexpensive disposable tray for mixing and dispensing dental bonding liquid materials.

BACKGROUND OF THE INVENTION

In the practice of dentistry, it is common to use epoxy type or multiple component bonding liquids and sealants, as well as single component types. The multiple component bonding liquids and sealants are mixed and applied to the teeth with a brush. These bonding liquids and sealants are typically supplied to the dentist in small, squeeze bottles. The liquids contained in the squeeze bottles are dispensed a drop at a time. The bonding liquids and sealants are supplied to the dentist usually in two components each contained in a small squeeze bottle. The at least two components in multiple component material must then be mixed to activate the bonding liquid and sealant for placement on the patient's tooth.

Mixing is done in a disposable tray having multiple, identical wells, a reusable tray, or on a paper pad. Each of these mixing platforms accomplish the function of mixing the bonding liquids and sealants, but not without some inconveniences for the dentist. The disposable trays having multiple identical wells performs well, but the use of bonding liquids and sealants having similar colored components often causes confusion during mixing. The use of reusable trays for mixing helps to prevent cross-contamination. Paper pads eliminate the risk of cross-contamination, but are difficult to use, especially with the less viscous bonding liquids and sealants. Additionally, none of the mixing trays provide a means to identify the dispensed liquid with the bottle from which it came. Therefore, once dispensed, should the dentist become momentarily interrupted, there is no way to determine the bottle from which the material has been dispensed.

Most of the bonding liquids and sealants are specialized chemical materials and, therefore, very expensive. Therefore, the dentist attempts to get every last drop from the bottle before discarding it. When the bottles are stored upright, it is often difficult to quickly dispense the relatively slow flowing liquid. Also, a uniform drop is not obtained unless a sufficient amount of liquid is present at the dispensing tip. This is because after being stored right side up, the liquid has settled at the bottom of the bottle, and when inverted for dispensing, a period of time is required for the liquid to flow into the dispensing tip. This is especially true when little liquid remains in the bottle.

Therefore, there is a need for a more convenient system to dispense dental bonding liquids and sealants having multiple component parts that must be mixed. There is also a need to dispense quickly and uniformly substantially all of the material within a bonding liquid and sealant bottle, as well as to prevent confusion between the different components once dispensed. This is applicable even for dental bonding liquids and sealants that do not have to be mixed, or are of a single component or part.

SUMMARY OF THE INVENTION

The present invention provides an improved dental tray for use by dentists in mixing and applying bonding liquids and sealants having one or multiple component parts. The present invention comprises a structure of a tray having multiple depressions in a top surface to hold a bottle of bonding liquid and sealant upside down during storage or prior to dispensing. The multiple depressions can hold bottles having caps of varying size. The depressions are lined up with mixing wells of distinctive shapes for each component of the bonding liquid or sealant or multiple applications of a single component bonding liquid or sealant. An indentation for holding the dental tray is positioned between the line of distinctive shaped wells to further separate the different components of the bonding liquid during mixing.

Accordingly, it is an object of the present invention to provide a convenient tray for mixing dental bonding liquids and sealants.

It is a further object of the present invention to prevent confusion between dispensed bonding liquids and sealants.

It is an advantage of the present invention that time is saved by the dentist in not having to wait until the liquid reaches the dispensing tip on the bottle of bonding liquid and sealant.

It is another advantage of the present invention that the last drop of bonding liquid and sealant can be used, therefore not wasting expensive material.

It is yet another advantage of the present invention that a more uniform drop is obtained and, therefore, a more consistent mixture due to liquid being readily available near the dispensing tip.

It is a feature of the present invention that multiple depressions are formed therein for holding various sized caps and bottles upside down.

It is yet another feature of the present invention that the distinctly shaped mixing wells are lined up with the depression holding the bottle and cap.

These and other objects, advantages and features will become readily apparent in view of the following more detailed description.

DETAILED DESCRIPTION OF THE PREFERRED EMBODIMENT

Figure 1:
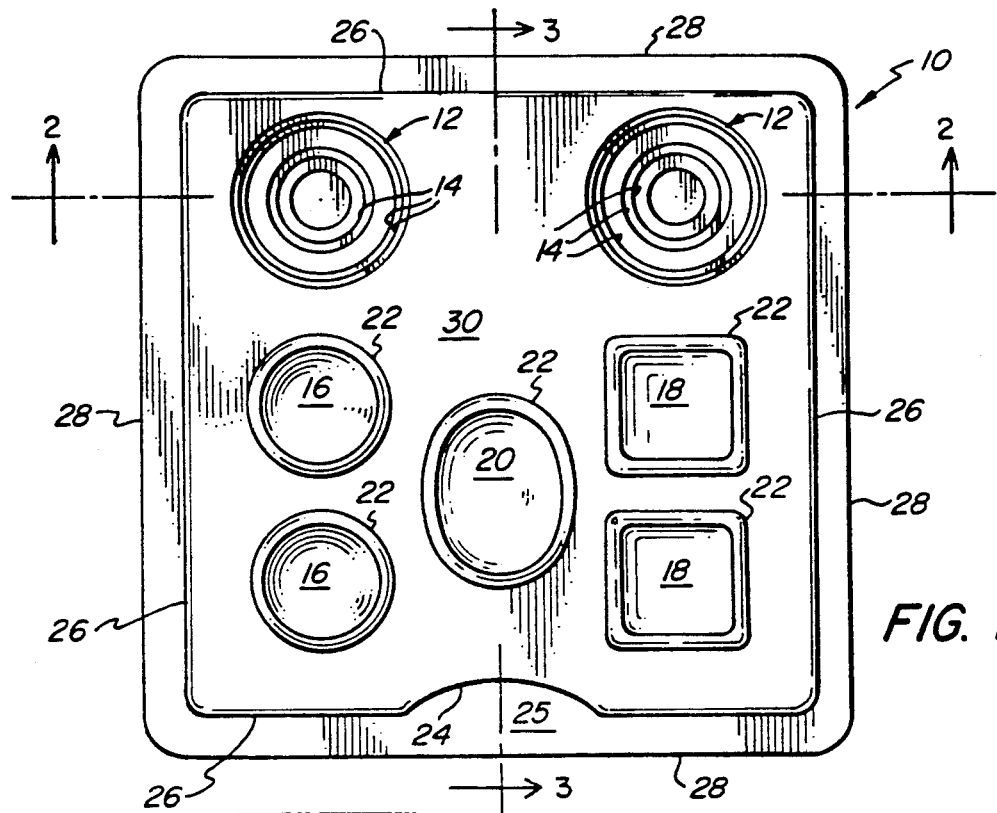
FIG. 1 is a top view of the present invention.

FIG. 1 illustrates the present invention. A rectangular dental tray 10 has two depressions 12 therein. Depressions 12 are circular and have concentric steps or rings 14 leading downward to the bottom. In line with one depression 12 and formed within top surface 30 are two round wells 16. Round wells 16 are generally hemispherical in shape and are adapted to receive dental material therein. The wells 16 have a raised rim 22 circumscribing the perimeter thereof. In line with the other depression 12 are two square wells 18. Square wells 18 form a generally square well in which material is placed. Square wells 18 have a raised rim 22 circumscribing the perimeter thereof. Positioned between the line of round wells 16 and the line of square wells 18 is an oval well 20. Oval well 20 is formed by a generally elliptical shaped well in which material can be placed and mixed. Oval well 20 also has a raised rim 22 circumscribing the perimeter thereof. Oval well 20 has a length greater than the longest length of each round well 16 or square well 18.

Adjacent each side of the top surface 30 of the dental tray 10 are sides 26 extending perpendicular therefrom. On the edge of sides 26 opposite surface 30 are lips 28, which extend perpendicularly from sides 26 parallel to top surface 30. The lips 28 provide rigidity and stability for the dental tray 10.

On the side adjacent both the round wells 16 and square wells 18 in line with the oval well 20 is a finger indentation 24. Finger indentation 24 is generally arcuate in shape. Finger indentation 24 provides a finger area 25 extending from lip 28. The finger area 25 provides a convenient area in which the dentist can hold the dental tray 10 during use and mixing. This also provides the dentist with an intuitive reference point from which different bonding components, if used, can very easily be referenced with very little attention from the doctor. This greatly facilitates the avoidance of any possible confusion between the component parts of the bonding liquids and sealants after dispensing, if a multiple component bonding liquid and sealant is used.

Figure 2:
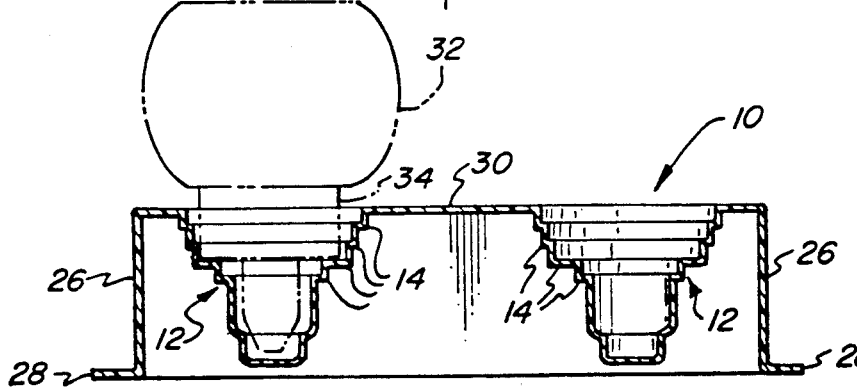
FIG. 2 is a cross section taken along line 2—2 in FIG. 1.

FIG. 2 illustrates the present invention in cross-section. A squeeze bottle 32, typical of the squeeze bottles in which dental bonding liquids and sealants are provided, is illustrated and positioned within depression 12. The shoulder of cap 34 can be seen resting on one of the concentric steps or rings 14. The diameters of the concentric steps 14 are selected to match a variety of cap 34 diameters. In this way, a variety of different bottles supplied by different manufacturers can be accommodated by the dental tray 10 of the present invention. With the dental tray 10 of the present invention, a variety of bottles 32 can be held upside down permitting the slow flowing bonding liquid and sealant to flow into the tip of the dispensing bottle 32. This assures that all of the relatively expensive liquid can be used without the inconvenience of having to wait for the liquid to flow into the tip during dispensing, as is typically the case when the bottle is stored in an upright position. Additionally, because a ready reservoir of liquid is available near the tip during dispensing, a more consistent drop or measure of bonding liquid and sealant can be obtained. This facilitates accurate measuring and therefore, better curing of multiple component bonding liquids and sealants.

Figure 3:
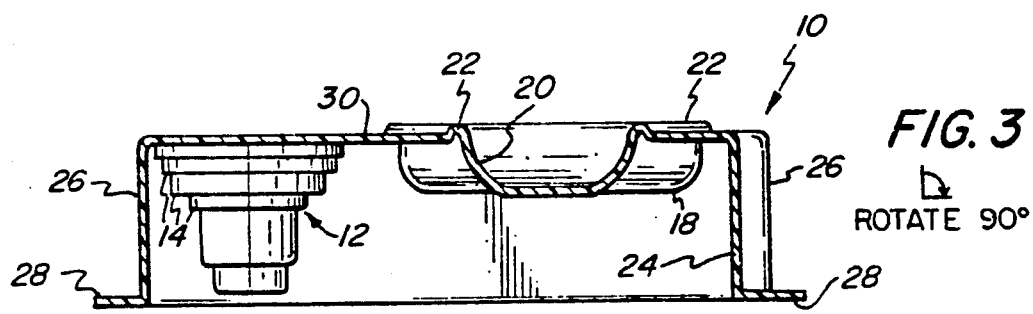
FIG. 3 is a cross section taken along line 3—3 in FIG. 1.

FIG. 3 is another cross-section of the dental tray of the present invention. FIG. 3 illustrates the general shape of the oval well 20. Additionally, FIG. 3 illustrates the raised rim 22. Raised rim 22 provides a convenient surface to wipe a mixing brush as well as prevent overflow onto the top surface 30. Raised rim 22 provides the additional function of defining the wells 16, 18 and 20 at a glance.

Figure 4:
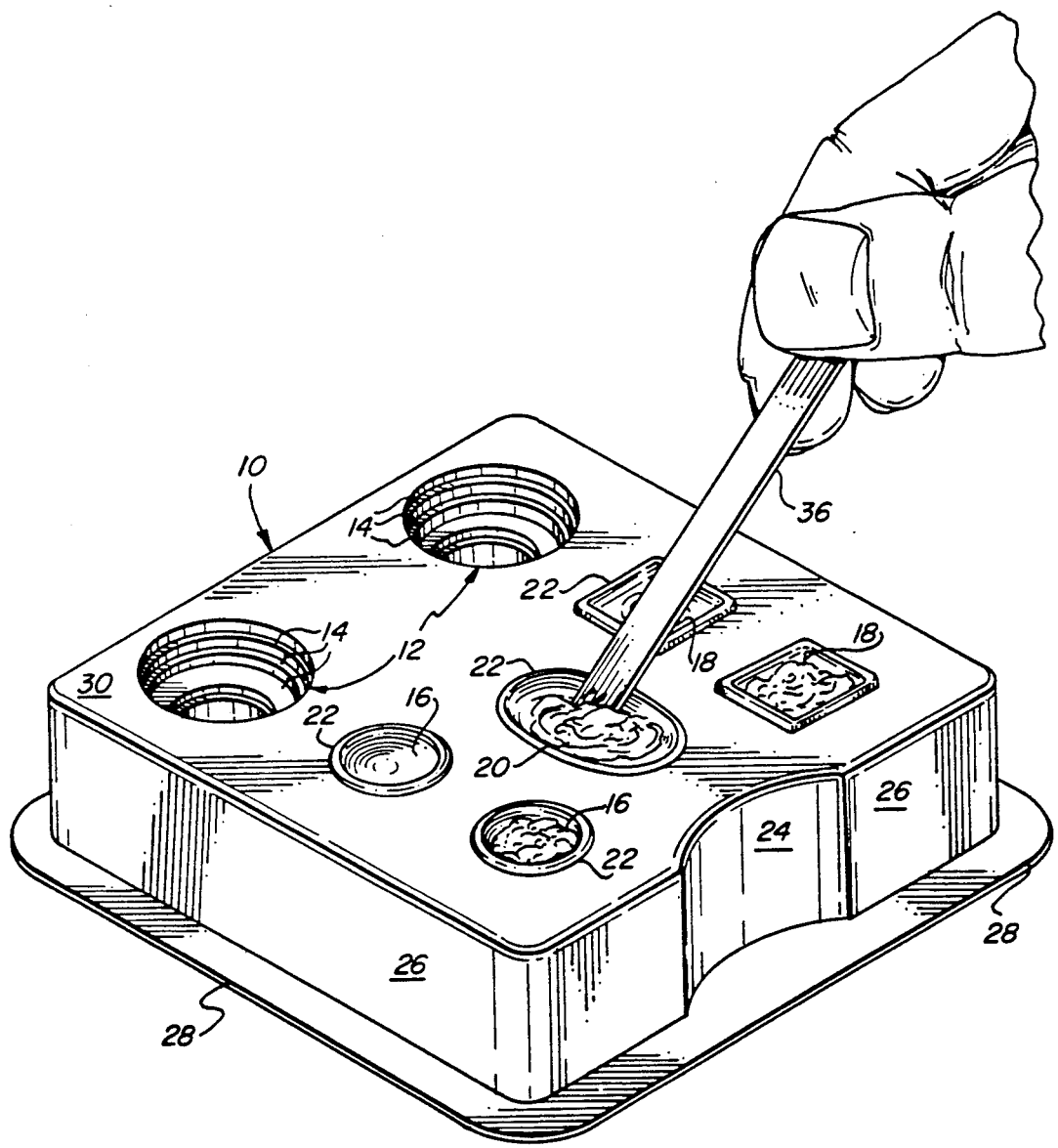
FIG. 4 is a perspective view illustrating the present invention.

FIG. 4 clearly illustrates the depressions 12 and their respective concentric steps 14. FIG. 4 additionally illustrates a method of mixing multiple component bonding liquids and sealants with a mixing tool 36. Mixing tool 36 can be a stick or a brush.

Figure 5:
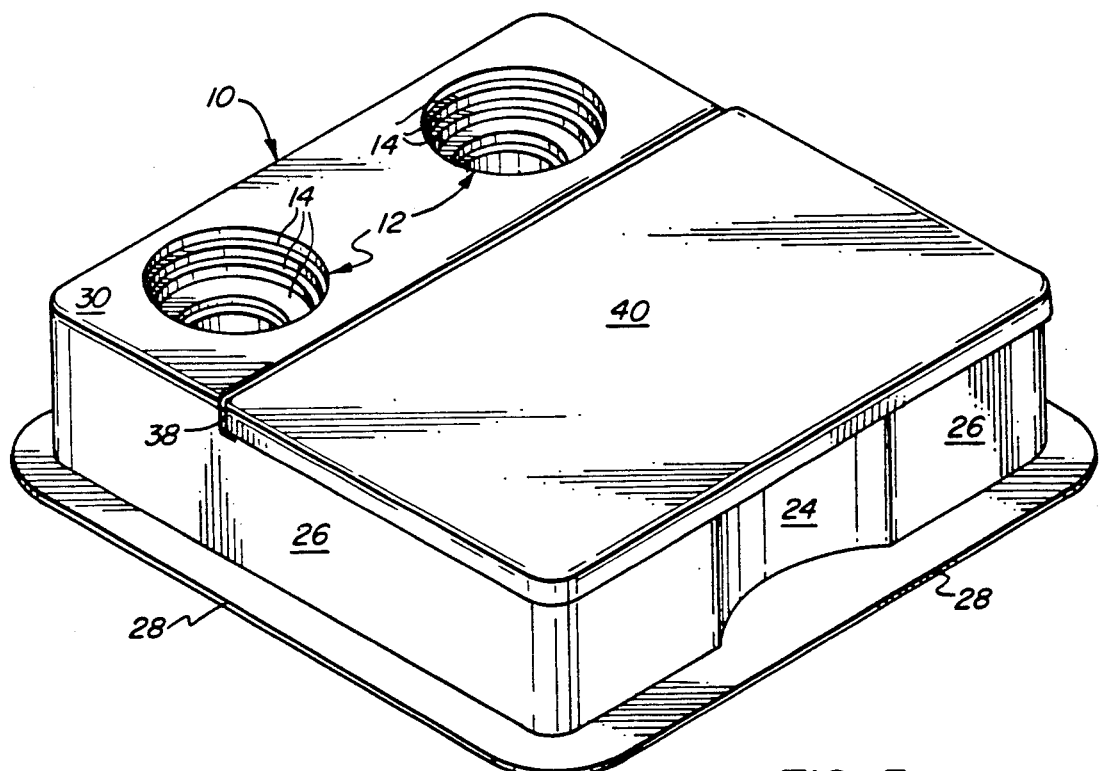
FIG. 5 is a perspective view of another embodiment of the present invention having a partial cover.

FIG. 5 illustrates another embodiment of the present invention. A groove 38 is formed in the top surface 30 of dental tray 10. The groove 38 is formed between the depressions 12 and the mixing wells 16, 18, and 20. A cover 40, which can be opaque depending on the dental bonding material being used, can be placed over the mixing wells 16, 18, 20. In this way bottles containing dental bonding liquids can be placed in the depressions 12 while the cover is placed on the dental tray 10. The cover helps to protect the mixing wells 16, 18, and 20 from contamination, such as dust. Additionally, if a light cured, typically single component, material is being used the working time of the bonding liquid and sealant can be extended by using an opaque cover between applications. The cover being fitted over sides 26 and in groove 38 provides for a source fit that will not unintentionally slide off, or let unwanted contaminants or light in.

With reference to FIGS. 1-5, the benefits of the present invention can readily be appreciated. The dental tray 10 of the present invention can be formed inexpensively from a thin plastic material. The anticipated disposable nature of the device makes inexpensive manufacture necessary. In use, when the dentist is about to perform a procedure requiring bonding liquids and sealants, the dentist places the necessary bottles containing the single or multiple component parts of the bonding liquid and sealant upside down into the depressions 12. The dentist can either store the bottles in this position until needed, or place them in the depressions 12 a short time prior to dispensing. This permits the liquid to flow into the tip of the bottle 12. Once the dentist is ready to preceed with the procedure requiring the bonding liquids or sealants, the dentist can place one component of the liquid in either circular well 16, and the other component of the liquid in either square well 18, if a multiple component material is being used. The two components can then be mixed with a tool 36 in oval well 20 prior to application. In the alternative, the dentist can mix the bonding liquids or sealants directly on an applicator brush by first dippling the brush in one distinctly shaped well containing the first component of the bonding liquid and then into the other distinctly shaped well containing the second component of the bonding liquid. Therefore, the dentist can maintain a supply of component parts of bonding liquids or sealants close to each other without becoming confused as to which well contains which component of the bonding liquid. This is especially helpful when the dentist performs multiple procedures within a short period of time, and thereby has several wells filled with liquid. The embodiment illustrated in FIG. 5 having the protective cover 40 is also helpful in avoiding contamination of the mixing wells 16, 18, and 20. Additionally, should a liquid bonding and sealant material be used having only one component the dentist can use the tray multiple times before having to throw the tray out. This effectively extends the useful life of the tray making its use more economical.

It should now be readily appreciated that the present invention provides a simple, inexpensive way for the dentist to simplify procedures using bonding liquids and sealants. This is accomplished in a simple device having a structure unlike anything available or disclosed prior to this invention.

This is only one embodiment illustrating the usefulness of the present invention, wherein it will be obvious to apply the teachings disclosed herein to other embodiments which may be made without departing from the spirit and scope of this invention.

What is claimed is:

1. A disposable tray for dental use comprising:
   a tray made of plastic;
   a plurality of depressions, each of said plurality of depressions having a large opening adjacent the top surface and successively smaller openings progressing downward from the top surface;
   a first plurality of wells formed within said tray having a first shape;
   a second plurality of wells formed within said tray having a second shape;
   a single mixing well formed within said tray between said first and second plurality of wells having a third shape; and
   a finger indentation means, formed within said tray between said first and second plurality of wells, permitting a user to hold said tray stationery during use.

2. A disposable tray as in claim 1, wherein said large and smaller openings are circular in shape.

3. A disposable tray as in claim 2, wherein:
   said first shape is circular;
   said second shape is square;
   said third shape is oval.

4. A disposable tray as in claim 3 further comprising:
   a raised rim circumscribing the perimeter of each of said first plurality of wells, second plurality of wells, and single mixing well.

5. A disposable tray as in claim 1 further comprising:
   a cover placed over said first and second plurality of wells.

6. A disposable tray as in claim 5 wherein:
   said cover is opaque.

7. A disposable plastic tray for mixing two part bonding liquids and sealants for dental use comprising:
   a plastic rectangular tray having a top surface;
   perpendicular sides extending from each edge of said top surface;
   a lip extending perpendicularly from the sides on the edge opposite the top surface;
   two circular depressions formed within the top surface having concentric circular steps of decreasing diameters extending downward from the top surface;
   two circular mixing wells, each having a raised rim formed in the top surface in line with one of said two circular depressions;
   two square mixing wells, each having a raised rim, in line with the other of said two circular depressions;
   an oval mixing well having a length greater than the longest length of said two circular or square mixing wells, said oval mixing well formed within said tray between the line of said two circular mixing wells and the line of said two square mixing wells; and
   an arcuate finger indentation formed in the center of the side adjacent said oval mixing well.

8. A tray for dental use comprising:
   a tray;
   a plurality of depressions, each of said plurality of depressions having a large opening adjacent the top surface and successively smaller openings progressing downward from the top surface and of a size adapted to receive any of several predetermined bottle caps; and
   a plurality of adjacent wells formed within the top surface of said tray,
   whereby at least one bottle of liquid dental material can be placed upside down within one of said plurality of depressions and the liquid therein can be readily dispensed within at least one of said plurality of wells for mixing.

9. A dental tray as in claim 8, further comprising
   an opaque cover adapted to fit over said plurality of wells.

10. A dental tray as in claim 9 wherein:
    said tray and said cover are made of plastic.

11. A disposable tray for dental use comprising:
    a tray;
    a plurality of depressions, each of said plurality of depressions having a large opening adjacent the top surface and successively smaller openings progressing downward from the top surface;
    a first plurality of wells formed within said tray having a first shape;
    a second plurality of wells formed within said tray having a second shape; and
    a single mixing well formed within said tray between said first and second plurality of wells having a third shape.

12. A disposable tray for dental use as in claim 11, further comprising:
    an opaque cover adapted to fit over said first and second plurality of wells and said mixing well.

* * * * *